United States Patent [19]

Saito

[11] Patent Number: 4,827,760

[45] Date of Patent: May 9, 1989

[54] APPARATUS FOR MEASURING THE MASS OF PARTICULATES

[75] Inventor: Keizo Saito, Tsuchiura, Japan

[73] Assignees: Agency of Industrial Science & Technology; Ministry of International Trade & Industry, both of Tokyo, Japan

[21] Appl. No.: 174,370

[22] Filed: Mar. 28, 1988

[30] Foreign Application Priority Data

Apr. 17, 1987 [JP] Japan .................................. 62-96019

[51] Int. Cl.$^4$ .......................................... G01N 15/00
[52] U.S. Cl. ...................................... 73/28; 73/864.71
[58] Field of Search ............ 73/28, 23, 863.11, 863.12, 73/863.23, 864.71, 865.5, 580

[56] References Cited

U.S. PATENT DOCUMENTS

| | | | |
|---|---|---|---|
| 4,257,258 | 3/1981 | Bovenlander | 73/23 |
| 4,580,441 | 4/1986 | Sakurai et al. | 73/28 |
| 4,633,706 | 1/1987 | Ito et al. | 73/28 |
| 4,747,297 | 5/1988 | Okayama et al. | 73/28 |

Primary Examiner—Stewart J. Levy
Assistant Examiner—Joseph W. Roskos
Attorney, Agent, or Firm—Oblon, Fisher, Spivak, McClelland & Maier

[57] ABSTRACT

An apparatus for measuring the mass of particulates is disclosed. A low-temperature filter which is held at a temperature lower than the boiling point of the particulate liquid component contained in gas, and a high-temperature filter, which is held at a temperature higher than the boiling point of the liquid component but lower than the ignition point of the solid component of the particulates, are oscillated while they are contacted by a sample gas at the same rate. The mass of all particulates deposited on the low-temperature filter and the mass of the particulate solid component deposited on the high-temperature filter are calculated from each inherent oscillation frequencies of the two filters, while the mass of the liquid component is obtained by subtracting the mass of the solid component from the mass of the total particulates.

5 Claims, 2 Drawing Sheets

APPARATUS FOR MEASURING THE MASS OF PARTICULATES

BACKGROUND OF THE INVENTION

1. Field of the Invention

This invention relates to an apparatus for measuring the mass of particulates, which is used for the measurement or control of the concentration of particulates contained or dispersed in smoke exhausted from diesel engines, gas turbines, etc.

2. Prior Art Statement

In recent years, environmental pollution has become a serious social problem, and it is necessary to control the concentration of particulates in smoke exhausted from diesel engines, gas turbines, stirling engines, etc. through control of exhaust conditions.

Particulates in exhaust smoke mainly consist of dry soot in solid phase and sof in liquid phase. The solid component mainly consists of carbon black, while the liquid component consists of uncombusted fuel and lubricant and is whitish in color and not noticeable. Therefore, when exhaust conditions are controlled with the amount of dry soot as a criterion of the particulate concentration of the exhaust, there are cases in which an exhaust gas having light color and low dry soot concentration indicates an increased liquid component resulting from reduction of the solid component. In this case, it is necessary to measure the mass of the solid component and that of the liquid component separately for obtaining accurate control. Besides the case of exhaust smoke control, there are also other cases in measurement, regulation, research, etc. where it is necessary to measure separately the masses of the solid and liquid components of particulates dispersed in gas.

One technique for measurement of the mass of particulates is the oscillating microbalance method (U.S. Pat. No. 4,391,338). In this method, the total mass of particulates is obtained by capturing the particulates on a filter at a room temperature (i.e., 50° C.) close to normal temperature, oscillating the filter with the particulates deposited thereon using an oscillator and measuring an inherent frequency change corresponding to the deposited amount of particulates.

While in this prior art technique the total mass of the particulates is obtained, the masses of solid and liquid components cannot be measured separately.

OBJECT AND SUMMARY OF THE INVENTION

This invention has been accomplished in the light of the above, and its object is to provide an apparatus for measuring the mass of particulates which permits real-time measurements of the masses of the solid and liquid components of particulates.

To attain the above object of the invention, there is provided an apparatus for measuring the masses of the particulate solid and liquid components in gas, which apparatus comprises a particulate-capturing unit including a low-temperature filter held at a temperature lower than the boiling point of the liquid component and a high-temperature filter held at a temperature higher than the boiling point of the liquid component but lower than the ignition point of the solid component, two variable oscillators for oscillating the respective low- and high-temperature filters, two counters for respectively reading out each inherent oscillation frequencies of the low- and high-temperature filters and a data-processing unit for calculating the masses of the solid and liquid components from each inherent oscillation frequency read out by the counters.

According to the invention, both solid and liquid particulate components in gas under measurement are captured by the low-temperature filter, while only the solid component is captured by the high-temperature filter. Thus, the mass of particulates captured by the low-temperature filter and that captured by the high-temperature filter are obtained from each inherent oscillation frequency of the two filters being oscillated at non-restraining mode. The mass of the liquid component is obtained by subtracting the latter from the former.

According to the invention, it is thus possible to measure the solid and liquid components individually in real time, and conditions of exhausting smoke can be controlled continuously through measurement of instantaneous changes in the contents of the two components over a lapse of time.

The above and other objects and features of the invention will become more apparent from the following detailed description with reference to the accompanying drawings.

DETAILED DESCRIPTION OF THE PREFERRED EMBODIMENT

Figure 1:
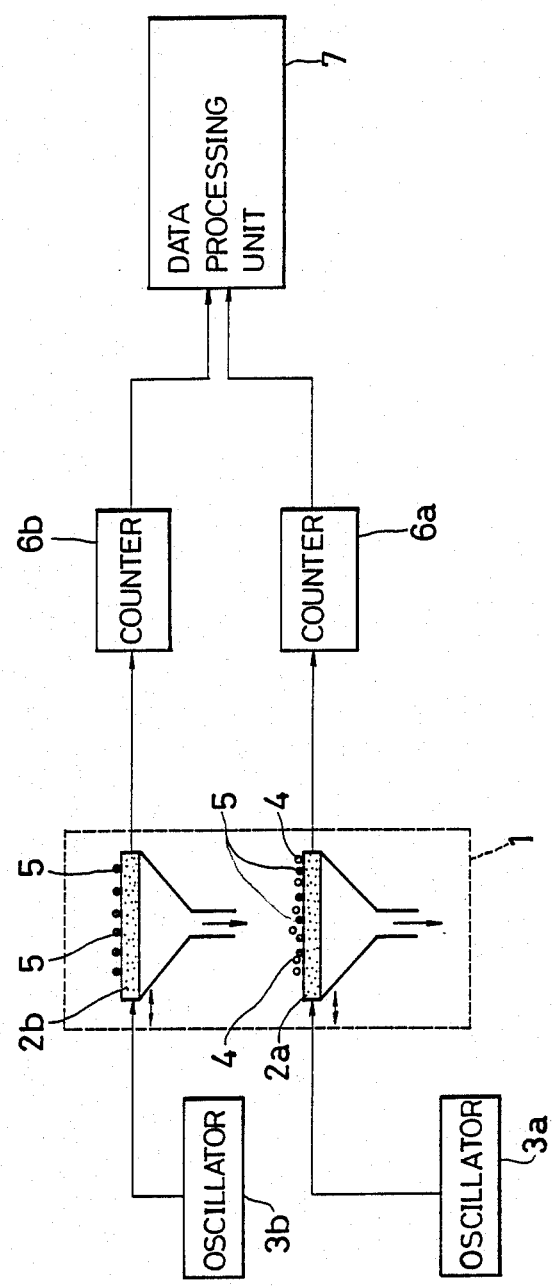
FIG. 1 is a schematic representation of an embodiment of the apparatus for measuring the mass of particulates according to the invention.

Referring now to FIG. 1, there is shown an apparatus for measuring the mass of particulates. The illustrated apparatus comprises a particulate-capturing unit 1 including a low-temperature filter 2a and a high-temperature filter 2b, oscillators 3a and 3b, counters 6a and 6b and a data-processing unit 7. The low-temperature filter 2a is temperature controlled to within a temperature range $T_1$ lower than the boiling point of a liquid component 4 of particulates in a dispersion medium to be measured (e.g., within a temperature range from normal room temperature to about 50° C. in the case where the dispersion medium is diesel exhaust smoke). On the other hand, the high-temperature filter 2b is temperature controlled to within a temperature range $T_2$ higher than the boiling point of the liquid component 4 but lower than the ignition point of a solid component 5 (e.g., 250° to 300° C. in the aforenoted case of diesel exhaust smoke).

The low- and high-temperature filters 2a and 2b are of the same weight, size and material. They preferably exhibit excellent high temperature characteristics and detection sensitivity in the detection of changes in the oscillation frequency with changing mass and are preferably thin film filters made from, e.g., ceramic or glass fiber.

It is to be understood that the two filters 2a and 2b are entirely the same except for the temperature conditions noted above. They are disposed in a capturing tube (not shown) through which a sample gas to be measured is caused to flow, the sample gas being withdrawn from the outlet side of the capturing tube to be supplied to the surfaces of both the filters in the same concentration and at the same rate.

Examples of the sample gas to be measured are exhaust gases from various combustion apparatuses, e.g., diesel engines and gas turbines, and particulate-containing air in a flue or a smoke duct.

The oscillators 3a and 3b are connected to the respective low- and high-temperature filters 2a and 2b. The filters 2a and 2b can be oscillated by the oscillators 3a and 3b.

Counters 6a and 6b are connected to the respective low- and high-temperature filters 2a and 2b. These counters 6a and 6b read out the oscillation frequencies of the low- and high-temperature filters 2a and 2b, and their outputs are supplied to the data-processing unit 7.

The data-processing unit 7 calculates the masses of particulates captured by the filters 2a and 2b from each inherent frequency of the low- and high-temperature filters 2a and 2b as provided from the counters 6a and 6b, and it records the calculated mass values. It is further capable of calculating the difference between and the ratio of two numbers.

The mass of the particulates deposited on a filter after the lapse of a predetermined period of time from the start of measurement is calculated as follows.

The increment $\Delta m$ of the mass of particulates after the lapse of the predetermined period of time from the start of measurement, is given as $$\Delta m = m_2 - m_1 \quad (1)$$
$$= kf_2^{-2} - kf_1^{-2}$$
$$= k(f_2^{-2} - f_1^{-2})$$

where $m_1$ is the mass of particulates at the time of the start of measurement, $m_2$ is the mass of particulates after the lapse of a predetermined period of time, $f_1$ is the inherent oscillation frequency of the filter at the time of the start of measurement, $f_2$ is the inherent oscillation frequency of the filter after the lapse of the predetermined period of time, and K is a proportionality constant.

In order to determine the respective masses of the solid and liquid components 5 and 4 of particulates in a gas sample, the low- and high-temperature filters 2a and 2b of the capturing unit 1 are held at their respective predetermined temperatures noted and above are disposed in a sample gas passage such that the sample gas is supplied to them in the same concentration and at the same rate. These filters 2a and 2b are oscillated by the oscillators 3a and 3b. The counters 6a and 6b read out the inherent oscillation frequencies and supply the values thereof to the data-processing unit 7.

As the sample gas is supplied to the capturing unit 1, both the solid and liquid components 5 and 4 of particulates in the sample gas are captured and deposited on the low-temperature filter 2a, but the liquid component 4, although it is once captured in the high-temperature filter 2b, is not deposited on this filter because it is instantly evaporated, and only the captured solid component 5 is deposited in this filter 2b.

Since the filters 2a and 2b are of the same specifications except for temperature and are supplied with the sample gas under measurement in the same concentration and at the same rate, it may be assumed that an equal mass of solid component 5 is captured in both the filters 2a and 2b. This means that the difference between the masses of solid component 5 captured by the two filters 2a and 2b, corresponds to the mass of liquid component 4 on the low-temperature filter 2a.

As has been shown, while the sample gas is supplied at a predetermined rate to the capturing unit 1, the counters 6a and 6b read out changes in each inherent oscillation frequency of the filters 2a and 2b and continuously supplies this frequency data to the data-processing unit 7.

The data-processing unit 7 performs calculations from each inherent oscillation frequency of the two different filters before and after the capturing of particulates on the basis of equation (1). More specifically, it calculates the mass of the deposited particulates, i.e., the sum $W_a$ of the masses of the solid and liquid components 5 and 4, from the output of the counter 6a, and calculates the mass $W_b$ of the solid component 5 from the output of the counter 6b. The mass of the liquid component 8 is determined by subtracting the mass $W_a$ of the solid component from the sum $W_b$ of the masses of the solid and liquid components.

It is thus possible to calculate the contents of the solid and liquid components 5 and 4 per unit measurement time provided that the rate of supply of the sample gas under measurement to the two filters 2a and 2b is known.

Further, by causing oscillation of the two filters 2a and 2b while supplying the sample gas thereto, it is possible to determine the sum $W_a$ of the masses of solid and liquid components, mass $W_b$ of solid component and mass $W_a - W_b$ of liquid component of particulates deposited on the filters from the instantaneously varying inherent oscillation frequencies and continuously obtain the real-time instantaneously varying contents.

Figure 2:
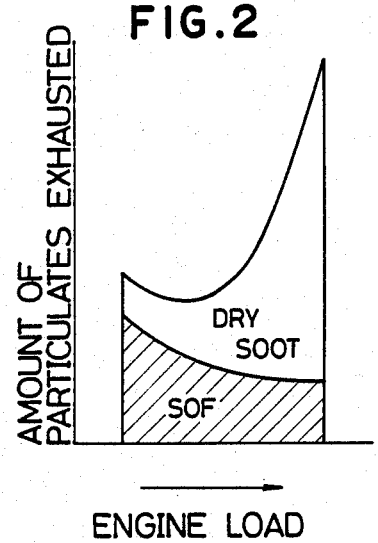
FIG. 2 is a graph showing the relation of the amounts of sof and dry soot contained in diesel exhaust in relation to engine load.

FIG. 2 is a graph showing an example of the relation between dry soot, which consists of solid particles among particulates which in diesel exhaust smoke, and sof consisting of liquid particles among the particulates correspond to the engine load. It will be seen from the graph that a great amount of sof is contained in excess of the amount of dry soot even under a low engine load, at which time the exhaust gas color is pale.

Figure 3:
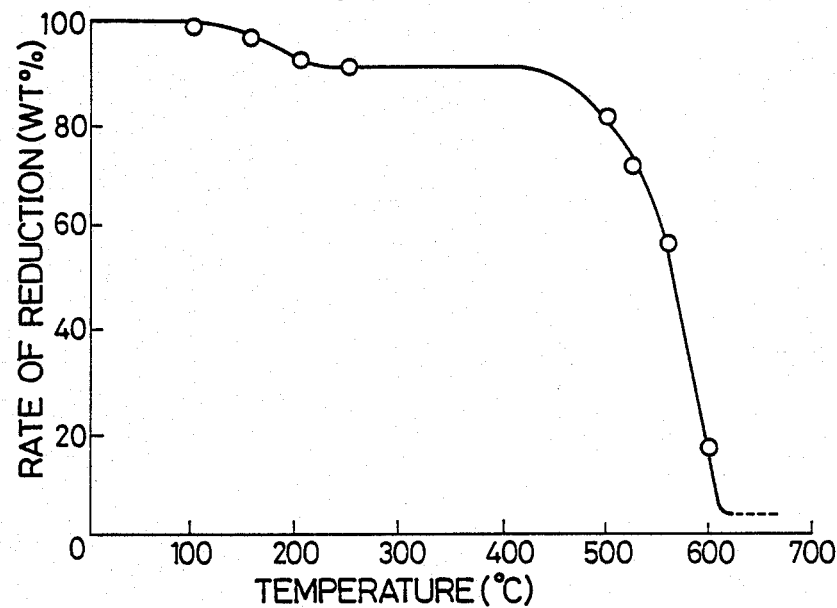
FIG. 3 is a graph showing the rate of reduction of particulates in exhaust gas plotted against temperature.

FIG. 3 is a graph showing the rate of reduction, plotted against temperature, of total particulates in diesel exhaust gas (the atmospheric oxygen concentration being 21%).

The contained amount of particulates peaks and declines when the temperature reaches about 150° C., being less by about 10% by weight at about 250° C., being sharply down when the temperature exceeds 400° C. and becoming less than 10% by weight when the temperature exceeds 600° C.

Figure 4:
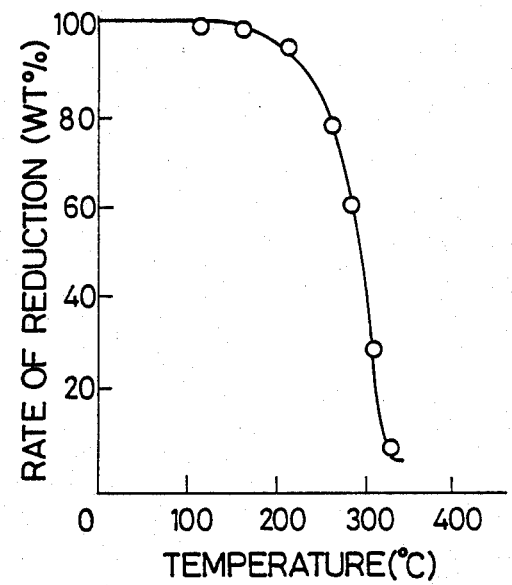
FIG. 4 is a graph showing the rate of reduction of sof in the particulates plotted against temperature.

FIG. 4 is a graph showing the rate of reduction, plotted against temperature, of sof extracted from the exhaust gas noted above (the atmospheric oxygen concentration being 21%). The sof content is reduced when a temperature of 150° C. is reached and becomes less than 10% by weight when the temperature exceeds 300° C.

It will be seen from the above two graphs that when a temperature of 150° C. is reached the amount of particulates peaks and declines with commencement of evaporation of the sof component, and when a temperature of about 300° C. is reached the sof component is evaporated almost entirely, so that the particulate amount is reduced by about 10% by weight. At this moment, the remaining particulates substantially consist of dry soot. When the temperature reaches 500° C., the dry soot begins to decline because of combustion. When the temperature exceeds 600° C., the dry soot is combusted almost entirely, that is, the residual amount becomes less than 5% by weight. Therefore, when measuring the masses of the solid and liquid components of particulates in the diesel exhaust gas, by setting and maintaining the temperature of the low-temperature filter to be 100° C. or below and the temperature of the high-temperature filter in the neighborhood of 400° C., particulates in the exhaust gas are entirely deposited on the low-temperature filter while only dry soot is substantially deposited on the high-temperature filter. Thus, the mass of the liquid component of particulates can be measured readily, accurately and in real time by determining the masses of both the solid and liquid components from each inherent oscillation frequency of both filters and subtracting the latter from the former.

As has been described in the foregoing, according to the invention it is possible to obtain an apparatus for measuring the mass of particulates which permits measurements of the masses of the solid and liquid components of particulates in gas separately and in real time and also permits instantaneous control of contents of both the components through measurement of changes in the contents of the two components over a lapse of time.

What is claimed is:

1. An apparatus for measuring the masses of particulate solid and liquid components in gas, comprising:
   a particulate-capturing unit including a low-temperature filter held at a temperature lower than the boiling point of the liquid component and a high temperature filter held at a temperature higher than the boiling point of the liquid component but lower than the ignition point of the solid component;
   one oscillator for oscillating said low-temperature filter and a second oscillator for oscillating said high-temperature filter;
   one counter for reading out each inherent oscillation frequency of said low-temperature filter and a second counter for reading out each inherent oscillation frequency of said high-temperature filter; and
   a data-processing unit for calculating the masses of said solid and liquid components from said each inherent oscillation frequency read out by said one counter and from said each inherent oscillation frequency read out from said second counter.

2. The apparatus according to claim 1, wherein said data-processing unit calculates the mass of the liquid component from the difference between the masses of the solid and liquid components as obtained from the oscillation frequency of said low-temperature filter and the mass of the solid component as obtained from the oscillation frequency of said high-temperature filter.

3. The apparatus according to claim 1, wherein said low-temperature filter is held at a temperature in a range from normal room temperature to 100° C. while said high-temperature filter is held at 400° C.

4. The apparatus according to claim 1, wherein said low- and high-temperature filters are thin film ceramic filters.

5. The apparatus according to claim 1, wherein said low- and high-temperature filters are thin film glass fiber filters.

* * * * *